United States Patent [19]

Ammende et al.

[11] Patent Number: 5,122,254

[45] Date of Patent: Jun. 16, 1992

[54] SOLID STATE ELECTRODE FOR THE DETERMINATION OF SODIUM ION CONCENTRATIONS IN SOLUTIONS

[75] Inventors: Sonja Ammende, Frankfurt am Main; Hartmut Erdmann, Steinbach; Heinz-Werner Etzkorn, Neu Anspach; Klaus Zucholl, Mannheim, all of Fed. Rep. of Germany

[73] Assignee: Battelle - Institut, e.V., Fed. Rep. of Germany

[21] Appl. No.: 348,013

[22] Filed: Jan. 23, 1989

Related U.S. Application Data

[63] Continuation of Ser. No. 121,915, Nov. 17, 1978, abandoned.

[30] Foreign Application Priority Data

Nov. 17, 1986 [DE] Fed. Rep. of Germany ........ 3639312

[51] Int. Cl.⁵ .............................................. G01M 27/26
[52] U.S. Cl. ...................................... 204/419; 204/422; 204/423
[58] Field of Search ................ 204/419, 1 A, 422, 423

[56] References Cited

U.S. PATENT DOCUMENTS 4,632,732  12/1986  Fog et al. ............................ 204/1 T

FOREIGN PATENT DOCUMENTS

| 2649716 | 5/1977 | Fed. Rep. of Germany ..... 204/1 A |
| 3240239 | 5/1983 | Fed. Rep. of Germany . |
| 2545003 | 11/1984 | France . |
| 1597493 | 9/1981 | United Kingdom . |
| 2102963 | 2/1983 | United Kingdom . |
| WO84/01769 | 5/1984 | World Int. Prop. O. . |
| WO84/01829 | 5/1984 | World Int. Prop. O. . |

OTHER PUBLICATIONS

D. J. Fray et al., J. Chem. Thermodynamics, 5, 7, 485-491, (1975).

Paul Hagenmuller et al., "Solid Electrolytes", pp. 406-407, (1978).

P. Fabry et al., Sensors and Actuators, "Nasicon, an Ionic Conductor for Solid-State Na+ Selective Electrode", Band 15, Nr. 1, pp. 33-49 (Sep. 1988).

*Primary Examiner*—John Niebling
*Assistant Examiner*—Bruce F. Bell

[57] ABSTRACT

A solid state electrode for the determination of sodium ion concentrations in solutions, with a solid state electrolyte having a high conductivity for sodium ions being provided as the sodium sensitive membrane. The solid state electrode and a reference electrode forms a sensor.

The advantages of the sensor of invention are, in particular, high selectivity combined with economical production in thick-film technology. The sensor may be constructed in cylindridcal form.

5 Claims, 1 Drawing Sheet

SOLID STATE ELECTRODE FOR THE DETERMINATION OF SODIUM ION CONCENTRATIONS IN SOLUTIONS

This application is a continuation of application Ser. No. 121,915, filed Nov. 17, 1987.

BACKGROUND OF THE INVENTION

1. Field of the Invention

The present invention relates to a solid state electrode for the determination of sodium ion concentrations in solutions.

2. Technology Review

Glass membrane electrodes to measure sodium ion concentration are known, but these are expensive to manufacture. They are also fragile and sensitive to breaking and have a disadvantageously high cross sensitivity, for example for $H^+$, $Li^+$ and $K^+$. In addition, glass membrane electrodes become somewhat sensitive to the alkali metals at pH values greater than 10. Thus, in a solution that is 1.0F in sodium ion, a negative error of nearly 1 pH unit is obtained at a pH of 12. Moreover, the glass membrane electrodes have a relatively high membrane resistance, up to about 500 megaohms. The measuring technology as a whole is complicated and sensitive to interference.

SUMMARY OF THE INVENTION

The invention provides a solid state electrode for a sensor for the determination of sodium ion concentration in solution, comprising a sodium sensitive membrane consisting essentially of a solid state electrolyte having a high sodium ion conductivity of more than $10^{-6}$ Siemens/cm at room temperature.

It is an object of the invention to provide a solid state electrode for the determination of sodium ion concentrations in solutions and, more particularly, a sensor equipped with such a solid state electrode, with the solid state electrode being distinguished, in particular, by high selectivity for the sodium ions combined with a low cross sensitivity to other ions, particularly potassium ions, a noticeably reduced membrane resistance and a short response time. Moreover, the electrode and the sensor are economical to manufacture in large numbers, mechanically robust, able to be stored dry and also able to be manufactured with thick-film technology.

DETAILED DESCRIPTION OF THE INVENTION

Figure 1:
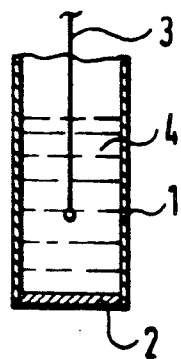
FIG. 1 is a schematic representation of a first embodiment of a sensor according to the invention employing a conventional reference electrode and an electrolyte.

FIG. 1 shows a conventional cylindrical housing 1 whose bottom is a membrane 2 of a sodium sensitive solid state electrolyte having high sodium ion conductivity. A conventional reference electrode 3 extends into the housing and dips into an electrolyte 4.

Figure 2:
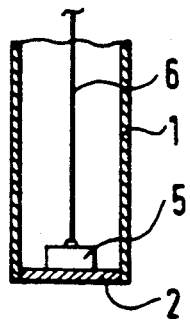
FIG. 2 is a schematic representation of a device similar to that of FIG. 1, with a solid state electrolyte membrane being employed and a solid state electrode.

The structure shown in FIG. 2 is similar, but here a solid state reference electrode 5 equipped with a lead-in wire 6 is employed.

Figure 3:
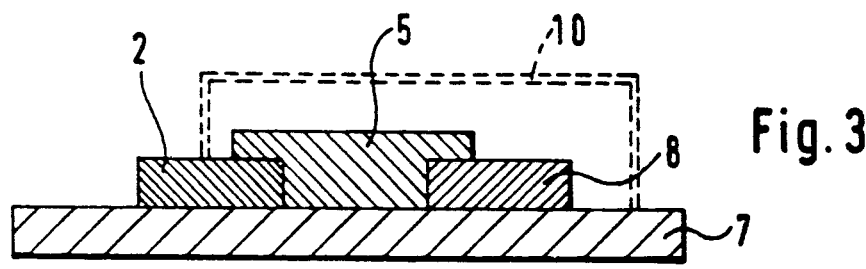
FIG. 3 shows the structure of a first embodiment constructed in thick-film technology.

FIG. 3 shows a first embodiment of the sensor in thick-film technology. In this case, the solid electrolyte membrane 2 is applied to a substrate 7 as is a contacting means 8 providing a conducting path. The solid state reference electrode 5 is also applied to the substrate 7, between membrane 2 and contacting means 8. Additionally, a cover 10 is provided which exposes part of the surface of membrane 2.

Figure 4:
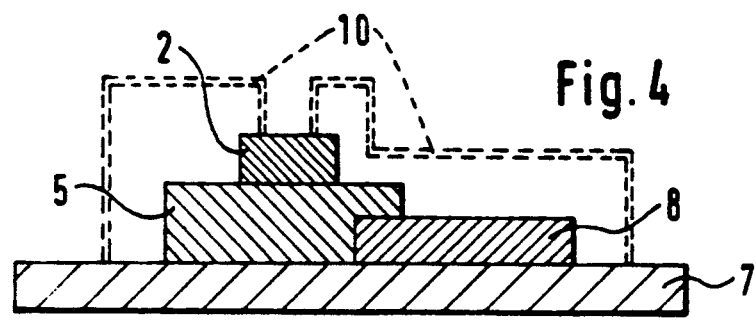
FIG. 4 shows a further structure, likewise in thick-film technology, in a second embodiment.

In the embodiment according to FIG. 4, which is also produced using thick-film technology, the solid electrolyte membrane 2 is applied to the upper side of the solid state reference electrode 5 and here again part of the surface of membrane 2 is not covered by the cover. Thick-film technology means a screenprinting process used usually in the electronic industry for hybrid fabrication.

The solid state reference electrode 5 is composed, for example, of sodium tungsten bronzes, sodium molybdenum bronzes, sodium or sodium alloys etc. (two-phase mixtures). For the solid electrolyte membrane 2, NASICON ™ of the formula $$Na_{1-x}Zr_2Si_xP_{3-x}O_{12}, \text{ where } 0 \leq x \leq 3$$

is preferred, with successful experiments having been performed with $x=2.0$ and 2.2. However, other $Na^+$ ion conductors are also suitable for this purpose, for example NASIGLAS ™ (amorphous NASICON-Type compounds), TITSICON ™ $Na_{3.1}Zr_{1.55}Si_{2.3}P_{0.7}O_{12}$, etc..

The present application relates to the subject matter disclosed in patent application No. P 36 39 312.6 filed Nov. 17th, 1986 in the Patent Office of the Federal Republic of Germany, the entire specification of which is incorporated herein by reference.

It will be understood that the above description of the present invention is susceptible to various modifications, changes and adaptations, and the same are intended to be comprehended within the meaning and range of equivalents of the appended claims.

What is claimed is:

1. A sensor for the determination of sodium ion concentration in solution, comprising:
a mechanically strong, solid state electrode prepared by screen printing including a sodium sensitive membrane consisting essentially of a solid state electrolyte of the formula $$Na_{1+x}Zr_2Si_xP_{3-x}O_{12}$$

having a sodium ion conductivity of more than $10^{-6}$ Siemens/cm at room temperature, and
a reference electrode applied directly to said solid state electrolyte by screen printing of a two-phase mixture selected from the group consisting of a sodium molybdenum bronze and a sodium tungsten bronze having a stable sodium ion activity.

2. The solid state electrode as set forth in claim 1, wherein $2.0 \leq x \leq 2.2$.

3. The sensor as set forth in claim 1 wherein said sodium sensitive membrane is of the formula $Na_{3.1}Zr_{1.55}Si_{2.3}O_{12}$.

4. The sensor for the determination of sodium ion concentration as set forth in claim 1, wherein said reference electrode consists essentially of a sodium molybdenum bronze.

5. A sensor for the determination of sodium ion concentration in solution, comprising:
a solid state electrode prepared by screen printing including a sodium sensitive membrane consisting essentially of a solid state electrolyte having a sodium ion conductivity of more than $10^{-6}$ Siemens/cm at room temperature, and
a reference electrode applied directly to said solid state electrolyte by screen printing a two-phase mixture selected from the group consisting of a sodium molybdenum bronze and a sodium tungsten bronze having stable sodium ion activity.

* * * * *

UNITED STATES PATENT AND TRADEMARK OFFICE
CERTIFICATE OF CORRECTION

PATENT NO. : 5,122,254
DATED : June 16, 1992
INVENTOR(S) : Sonja AMMENDE et al.

It is certified that error appears in the above-identified patent and that said Letters Patent is hereby corrected as shown below:

On the title page, Item [56] Other Publications

Please correct                         column 2, after

"Assistant Examiner - Bruce F. Bell" to include the following:

Attorney, Agent or Firm - Spencer & Frank

Signed and Sealed this

Twenty-fourth Day of August, 1993

Attest:

BRUCE LEHMAN

Attesting Officer       Commissioner of Patents and Trademarks